(12) United States Patent
Franciskovich et al.

(10) Patent No.: US 8,530,184 B2
(45) Date of Patent: Sep. 10, 2013

(54) METHOD FOR MONITORING A STERILIZATION PROCESS VIA MEMBRANE POTENTIAL

(75) Inventors: Phillip P. Franciskovich, Concord, OH (US); Tricia A. Cregger, Fairlawn, OH (US)

(73) Assignee: American Sterilizer Company, Mentor, OH (US)

( * ) Notice: Subject to any disclaimer, the term of this patent is extended or adjusted under 35 U.S.C. 154(b) by 63 days.

(21) Appl. No.: 13/162,073

(22) Filed: Jun. 16, 2011

(65) Prior Publication Data

US 2012/0021406 A1 Jan. 26, 2012

Related U.S. Application Data

(60) Provisional application No. 61/355,307, filed on Jul. 20, 2010.

(51) Int. Cl.
*C12Q 1/22* (2006.01)

(52) U.S. Cl.
USPC ............................................................ 435/31

(58) Field of Classification Search
USPC ................................................. 435/31, 287.4
See application file for complete search history.

(56) References Cited

U.S. PATENT DOCUMENTS

| | | | | |
|---|---|---|---|---|
| 7,416,883 B2 * | 8/2008 | Cregger et al. | ............ | 435/287.4 |
| 2005/0003396 A1 | 1/2005 | Ozkan et al. | | |
| 2007/0059788 A1 * | 3/2007 | Choi et al. | ...................... | 435/32 |
| 2007/0238145 A1 * | 10/2007 | Cote et al. | ........................ | 435/29 |
| 2010/0274500 A1 * | 10/2010 | Deutsch et al. | .................. | 702/19 |

FOREIGN PATENT DOCUMENTS

EP  1764417  3/2007

OTHER PUBLICATIONS

Lisle J. et al. The Use of Multiple Indices of Physiological Activity . . . Letters in Applied Microbiology 29:42-47, 1999.*
Berney M. et al. Flow Cytometric Study of Vital Cellular Functions in *E. coli* During Solar Disinfection. Microbiology 152(6)1719-1729, 2006.*
Bosshard F. et al. The Respiratory Chain is the Cells Achilles Heel During UVA Inactivation in *E. coli*. Microbiology 156(7)2006-2015, Jul. 2010.*
PCT/US2011/040701; PCT International Search Report and Written Opinion of the International Searching Authority dated Jan. 17, 2012.
L. Fiksdal et al: "Effect of u.v. light irradiation, starvation and heat on *Escherichia coli* beta-D-galactosidase activity and other potential viability parameters", Journal of Applied Microbiology, vol. 87, 1999, pp. 62-71.
PCT/US2011/040701; Annex to Form PCT/ISA/206; Communication Relating to the Results of the Partial International Search mailed Jan. 26, 2012.

* cited by examiner

*Primary Examiner* — Ralph Gitomer
(74) *Attorney, Agent, or Firm* — Renner, Otto, Boiselle & Sklar, LLP

(57) ABSTRACT

The disclosed invention relates to a method for monitoring a sterilization process. The method includes (A) exposing an article to be sterilized and a biological indicator to a sterilization medium during a sterilization process, the biological indicator comprising a cell with a plasma membrane; and (B) incubating the cell and measuring the membrane potential of the cell to detect change in the membrane potential.

21 Claims, 10 Drawing Sheets

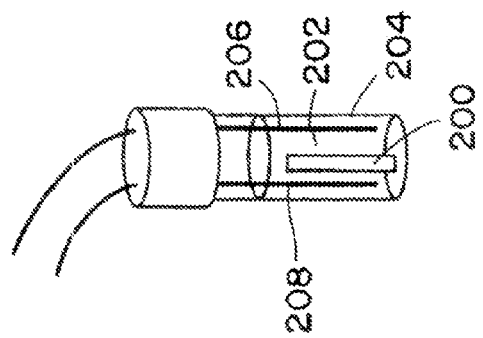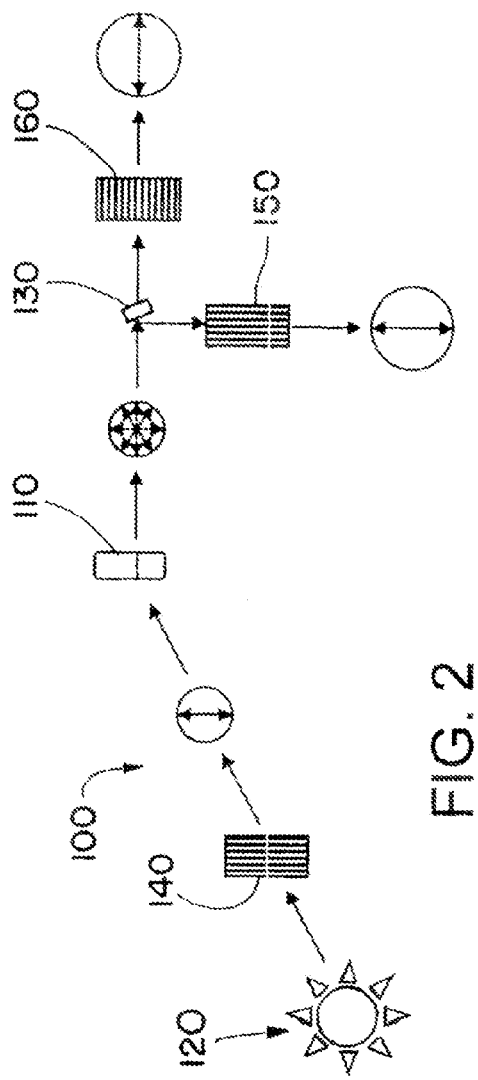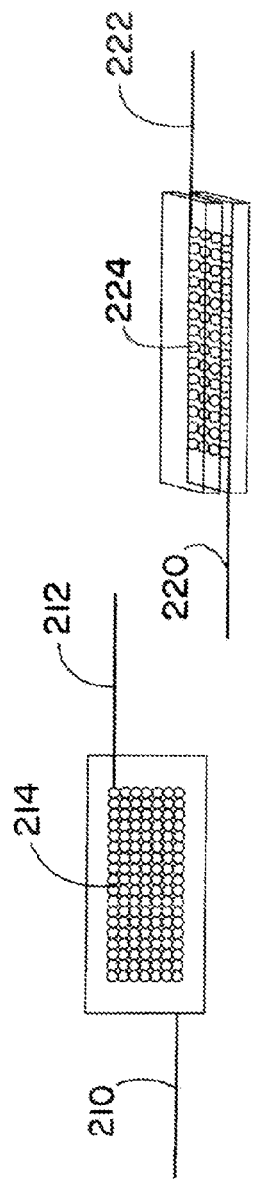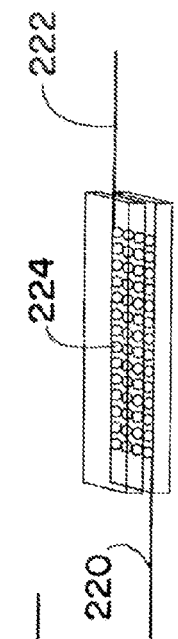

METHOD FOR MONITORING A STERILIZATION PROCESS VIA MEMBRANE POTENTIAL

CROSS-REFERENCE TO RELATED APPLICATION

The present application is related to and claims benefit under 35 U.S.C. §119(e) to U.S. Provisional Application No. 61/355,307, official filing date 20 Jul. 2010, the entirety of which is incorporated by reference.

TECHNICAL FIELD

This invention relates to a method for monitoring a sterilization process. More particularly, this invention relates to a method for monitoring a sterilization process wherein a biological indicator comprising a cell with a plasma membrane is exposed to the sterilization medium. The membrane potential of the biological indicator is then measured to detect the viability of the cell.

BACKGROUND

It is common to employ biological indicators such as bacteria in sterilization processes to determine whether an article to be sterilized has been exposed to an efficacious level of the active ingredient(s) of the sterilant. Biological indicators may be used to provide assurance that sterilization conditions are met within the processor or processed load itself. Biological indicators may be used to represent the worst case for the processing system by providing an extremely large number of organisms highly resistant to that particular process within or upon the indicator. Spores are often used as the organism of choice for monitoring such sterilization processes. Typically, users of biological indicators rely on the visible effects which would follow the multiplication of any surviving viable organism to determine the efficacy of the sterilization process in which the biological indicators are employed. This process may take hours to days to produce a visible change such as turbidity in an incubation medium or color change in a pH indicator if such an indicator is used.

Biological indicators have been proposed that correlate the activity of an endogenous (internally derived, preexisting) thermostable enzyme present within a spore coat to the actual viability of the organism. This has resulted in biological read times ranging from minutes to hours with a fluorometer or colorimeter. Although these biological indicators provide a correlation between the activity of the enzyme and the viability of the organism, the actual results obtained are due entirely to the activity of the enzyme and have no direct linkage to the viability of the organism.

Biological indicators have also been proposed that correlate the activity of an exogenous (externally derived, not previously existing) enzyme that is produced upon chemical induction of a recombinant gene if there are viable test organisms present after the sterilizing event being evaluated bearing that gene. This gives biological read times ranging from minutes to hours with a fluorometric read and provides a direct linkage to the viability of the organism.

SUMMARY

A problem with these earlier technologies relates to the fact that the prior art has mostly relied on the growth and division of organisms or the presence of enzymatic activity to detect viability. Growth and division of organisms can take hours to days to detect. Enzymatic activity can take minutes to hours to generate signals high enough to detect either fluorometrically or colorimetrically. Thus, there is a need for a method for achieving rapid results that are as definitive as those that are achieved using growth and division techniques. The present invention provides a solution to this problem.

This invention relates to a method, comprising: (A) exposing both an article to be sterilized and a biological indicator to a sterilization medium during a sterilization process, the biological indicator comprising cells with plasma membranes; and (B) measuring the membrane potential of the processed cells to detect any remaining viability within the population of cells following the completion of the sterilization process. This viability can be exemplified by but is not limited to membrane potential changes associated with ion flux events or the germination of the indicator spores.

The invention relates to a sterilization indicator which comprises an electrically conductive material positioned on a substrate, and a biological indicator (e.g., spores) positioned on part or all of the electrically conductive material.

This invention relates to a method for making a sterilization indicator, comprising: depositing an electrically conductive material on a substrate (e.g. using a printing method as exemplified by not limited to ink jet printing) and depositing a biological indicator (e.g., spores) on part or all of the electrically conductive material using, for example, an ink jet printer.

BRIEF DESCRIPTION OF THE DRAWINGS

FIG. 2 is a schematic illustration of a fluorescence polarizer.

FIG. 3 is a schematic illustration of a biological indicator used in conjunction with electronic monitoring of germination.

FIGS. 4 and 5 are illustrations of alternative biological indicators for evaluation of membrane potential through electrical signals.

DETAILED DESCRIPTION

Figure 1:
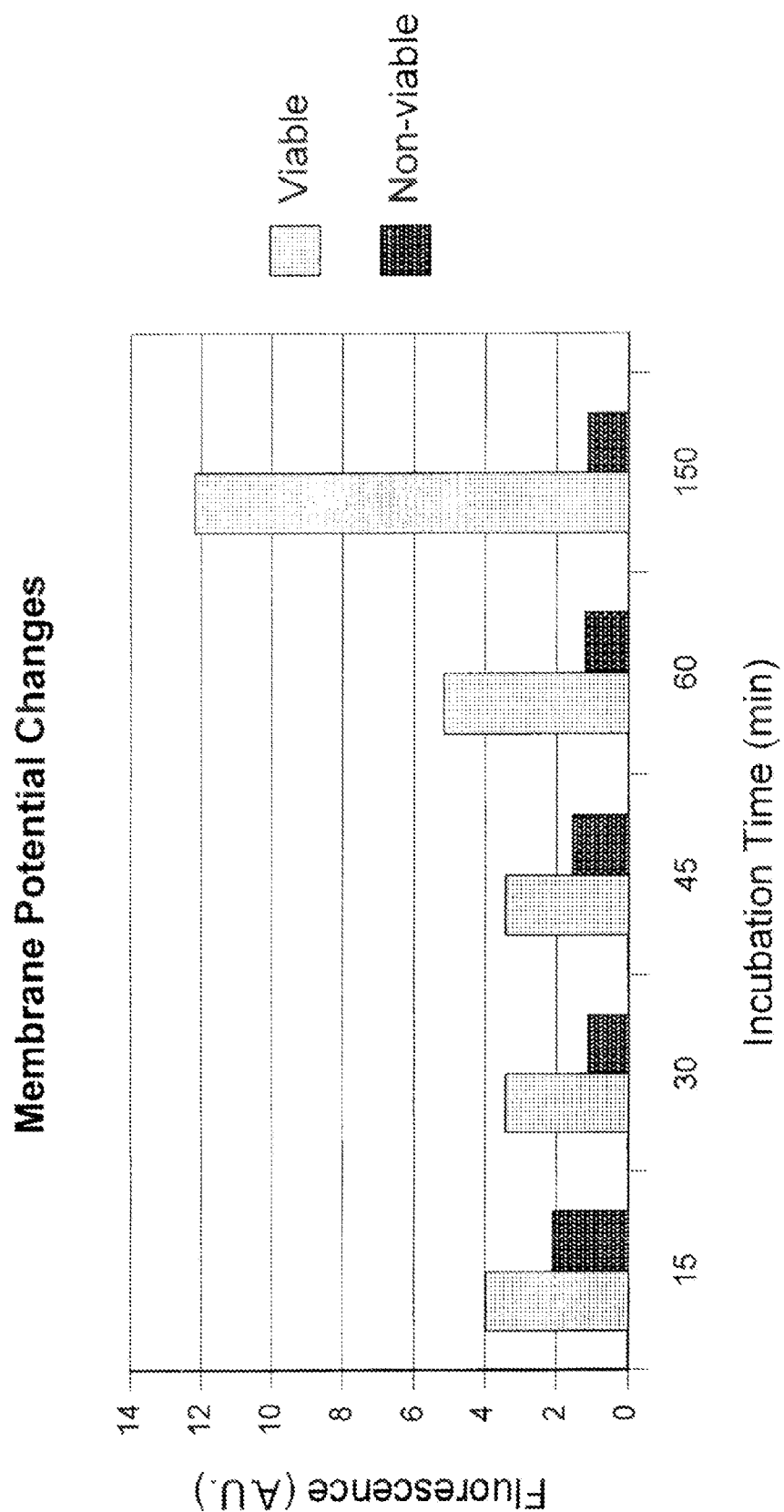
FIG. 1 is a plot showing the membrane potential changes for the spores tested in Example 1.

The term "sterilization" refers to rendering a substance incapable of reproduction, metabolism and/or growth. While this is often taken to mean total absence of living organisms, the term may be used herein to refer to a substance free from living organisms to a degree previously agreed or determined to be acceptable. Unless otherwise indicated, the term sterilization may be used herein to also refer to methods and procedures less rigorous than sterilization, for example, disinfection, sanitization, and the like.

The processes and apparatus described herein may be used in health care fields, scientific fields, and the like. These may be used in commercial and industrial applications where sterilization, disinfection, sanitization, decontamination, cleaning, and the like, may be desired. The commercial and industrial applications may include processes such as food processing, pasteurization, soil remediation, water remediation, and the like.

The sterilization process with which the inventive method may be used may comprise any sterilization process. The sterilization process may include sterilization processes wherein the sterilization medium or sterilant may comprise steam, dry heat, radiation, plasma, as well as one or more gaseous sterilants, one or more liquid sterilants, and the like. The radiation-based processes used may comprise an electron beam or any electromagnetic spectra including ionizing radiation, pulsed white or ultraviolet light, microwave, and the like. The radiation may comprise gamma or beta radiation. The gaseous sterilants may comprise ethylene oxide, gaseous hydrogen peroxide, and the like. The liquid sterilants may comprise formalin (formaldehyde gas dissolved in water and optionally containing methanol to inhibit the formation of toxic substances), glutaraldehyde, peracetic acid, liquid hydrogen peroxide, and the like. The biological indicator may be used to examine the lethality of sterilants against any microorganism with less resistance to the sterilization process than the test organism provided with the biological indicator. These microorganisms may include bacteria such as *Escherichia coli, Legionella* sp., *Campylobacter* sp., and other enteric bacteria, as well as *Staphylococcus* and *Streptococcus* species and other human pathogenic microorganisms such as *Cryptosporidium*. The biological indicator may comprise one or more test organisms. The test organism may comprise any cell with a plasma membrane whose resistance to the intended sterilization process exceeds that of the other organisms which the sterilization process is designed to destroy. The type of test organism used as the biological indicator may be dependent upon a variety of factors exemplified by, but not limited to, the type of sterilization process being used. The test organism may be a microorganism. The strains that may be used may be those that are the most resistant to the process used for sterilization. The test microorganism may comprise bacteria. The bacterial microorganisms may be those which form endospores, i.e., bacterial spores. The test organism may comprise bacteria of the *Bacillus* or *Clostridia* genera. The test organism may include *Geobacillus stearothermophilus, Bacillus atrophaeus, Bacillus subtilis, Bacillus sphaericus, Bacillus anthracis, Bacillus pumilus, Bacillus coagulans, Clostridium sporogenes, Clostridium difficile, Clostridium botulinum, Bacillus subtilis globigii, Bacillus cereus, Bacillus circulans, Escherichia coli*, or a mixture of two or more thereof.

The test organism may comprise fungi, mycobacteria, protozoa, vegetative bacteria, vegetative cells and/or their constituent parts and the like. Examples of fungi that may be used may include *Aspergillus niger, Candida albicans, Trichophyton mentagrophytes, Wangiella dermatitis*, and the like. Examples of mycobacteria that may be used may include *Mycobacterium chelonae, Mycobacterium gordonae, Mycobacterium smegmatis, Mycobacterium terrae*, and the like. Examples of protozoa that may be used may include *Giardia lamblia, Cryptosporidium parvum*, and the like. Examples of vegetative bacteria that may be used may include *Aeromonas hydrophila, Enterococcus faecalis, Streptococcus faecalis, Enterococcus faecium, Streptococcus pyrogenes, Escherichia coli, Klebsiella (pneumoniae), Legionella pneumophila, Methylobacterium, Pseudomonas aeruginosa, Salmonella choleraesuis, Helicobacter pylori, Staphylococcus aureus, Staphylococcus epidermidis, Stenotrophomonas maltophilia*, and the like. Organisms such as *Geobacillus stearothermophilus, Bacillus atrophaeus, Bacillus subtilis, Bacillus coagulans, Clostridium sporogenes*, and the like, may be used for determining the efficacy of moist heat sterilization (autoclaving), with *Geobacillus stearothermophilus* being especially useful.

The test organism may comprise *Aspergillus niger, Candida albicans, Trichophyton mentagrophytes, Wangiella dermatitis, Mycobacterium chelonae, Mycobacterium gordonae, Mycobacterium smegmatis, Mycobacterium terrae, Mycobacterium bovis, Mycobacterium tuberculosis, Giardia lamblia, Cryptosporidium parvum, Aeromonas hydrophila, Enterococcus faecalis, Streptococcus faecalis, Enterococcus faecium, Streptococcus pyrogenes, Escherichia coli, Klebsiella (pneumoniae), Legionella pneumophila, Methylobacterium, Pseudomonas aeruginosa, Salmonella choleraesuis, Helicobacter pylori, Micrococcus radiodurans, Deinococcus radiodurans, Staphylococcus aureus, Staphylococcus epidermidis, Stenotrophomonas maltophilia*, or a mixture of two or more thereof.

In addition to the test organisms selected on the basis of their acceptance as representing the most resistant organism (e.g. *Geobacillus stearothermophilus* and *Bacillus atrophaeus*), the biological indicator may further comprise agents of bioterrorism or biowarfare, e.g., *Bacillus anthracis* and the like. These resistant organisms may also comprise strains which have become resistant to formerly effective means of antibiotic treatment or chemical disinfection due to natural or man-made modifications. Examples of the former type may include VREs (Vancomycin Resistant *enterococci*), MSRAs (Methicillin Resistant *Staphylococcus aureus*), *Mycobacterium cheloni*, and the like. Such resistant organisms may be desirable because the VREs and MRSAs have recently developed resistance to therapeutic countermeasures (e.g., antibiotic resistance) and *M. cheloni* has developed resistance to some modes of disinfection (e.g., glutaraldehyde resistance), and thus provide suitable test organisms as "worst case" models.

In viable organisms such as bacteria, an electrical potential develops across the plasma membrane of the cell. This membrane potential plays a vital role in organism proton-motive forces required for activities such as the generation of adenosine triphosphate (ATP), chemotaxis, glucose transport, and survival of the organism at low pH. The establishment of a membrane potential is one of the first events that takes place as an organism begins to germinate or otherwise react to changes in the environment. The establishment of a membrane potential enables the cell to exchange material/information with its environment. Thus, by measuring membrane potential, the inventive method provides an instant or rapid read on cell viability.

Membrane potential in viable, actively metabolizing organisms may be high and cells with high membrane potential are often referred to as energized or hyperpolarized. Non-viable organisms and dormant organisms may exhibit low to zero membrane potential and are often referred to as de-energized or depolarized.

The inventive method may rely on changes in membrane potential that occur upon germination and growth of the test organism as a means of detecting viability of the test organism. When a viable organism is placed in conditions that favor germination and growth, the membrane potential of the organism may change. If, on the other hand, the organism is non-viable it would be unable to germinate and there would be no change in its membrane potential.

The biological indicator may comprise a genetically engineered biological indicator which may further comprise a reporter gene suitable for enhancing the membrane potential taken up by a test organism (e.g., a bacterial microorganism) using a suitable vehicle (e.g., plasmid or virus). Expression of the reporter gene may be actively blocked by a repressor gene. Expression of the reporter gene may remain blocked until the repressor gene is exposed to an inducer which may be present in a recovery medium. The test organism for use in a genetically engineered biological indicator may comprise any of the test organisms described above. In an embodiment, the test organism will not be exposed to the inducer until after the sterilization process has been completed, and consequently the indicator enzyme will not exist prior to or during sterilization. What may be exposed to the sterilization process are the various and vital mechanisms the test organism uses to survive and grow and which are also used for the production of the indicator enzyme. These may include the DNA polymerases used for cellular growth (and replication of the plasmid), RNA polymerases for transcription of the metabolic requirements of the test organisms (and the plasmid or virus borne reporter gene) and the ribosomal polysomes required for the translation of cellular proteins (as well as the expression of the indicator enzyme and or ion transport mechanisms).

There are two major classes of membrane potential fluorescent dyes, each class differing in their method of binding to the cell. The first class of membrane potential dyes, carbocyanines, may accumulate on hyperpolarized membranes and may be translocated into the lipid bilayer. A useful carbocyanine is 3,3'-dihexyloxacarbocyanine iodide [DiOC6(3)]. The second class of membrane potential dyes that may be used comprises the oxonols. The oxonol dyes may enter depolarized cells and bind to intracellular proteins or membranes. A useful oxonol dye is bis-(1,3-dibutylbarbituric acid)trimethine oxonol [DiBAC4(3)]. With carbocyanine dyes the fluorescence may increase with time and membrane potential, whereas with the oxonol dyes, the fluorescence may decrease with time and decreased membrane potential. The presence or absence of a membrane potential may then be directly associated with fluorescence over time.

The incubation medium may be referred to as a growth medium or as a recovery medium. The incubation medium may be in the form of a solid or a liquid. The incubation medium may comprise a particular buffered aqueous solution so that the biological indicator may be more sensitive to pH shifts, redox potentials, enzymatic activity, and the like.

The sterilization indicator may be used in any process wherein the sterilization indicator is exposed to a sterilization medium during a sterilization process and then to recovery and induction. The incubation medium may comprise one or more nutrient sources. The nutrient source may be used to provide energy for the growth of any of the test organisms that may survive the sterilization process. Examples of the nutrient sources may include pancreatic digest of casein, enzymatic digest of soybean meal, sucrose, dextrose, yeast extract, L-cystine, and mixtures of two or more thereof. A microbial growth indicator, which changes color or native state, in the presence of viable test organisms may be used with the incubation medium.

The incubation (recovery/induction) media may contain for example a membrane potential dye or voltage sensitive dye. The use of these microbial growth indicators may result in a change in fluorescence in response to a phenomenon of microorganism growth, such as changes in pH, oxidation-reduction potentials, enzymatic activity, as well as other indications of growth.

The incubation medium may further comprise one or more pH buffers, one or more neutralizers, one or more agents for maintaining osmotic equilibrium, or a mixture of two or more thereof. The pH buffers may include $K_2HPO_4$, $KH_2PO_4$, $(NH_4)_2HPO_4$, 2,2-Bis(hydroxymethyl)-2,2',2"-nitrilotriethanol (Bis Tris), 1,3-Bis[tris(hydroxymethyl)-methylamino] propane (Bis-Tris Propane), 4-(2-Hydroxyethyl)piperazine-ethanesulfonic acid (HEPES), 2-Amino-2-(hydroxymethyl)-1,3-propanediol (Trizma, Tris base), N-[Tris(hydroxymethyl)methyl]glycine (Tricine), Diglycine (Gly-Gly), N,N-Bis(2-hydroxyethyl)glycine (Bicine), N-(2-Acetamido)iminodiacetic acid (ADA), N-(2-Acetamido)-2-aminoethanesulfonic acid (aces), 1,4-Piperazinediethanesulfonic acid (PIPES), β-Hydroxy-4-morpholinepropanesulfonic acid (MOPSO), N,N-Bis(2-hydroxyethyl)-2-aminoethanesulfonic acid (BES), 3-(N-Morpholino) propanesulfonic acid (MOPS), 2-[(2-Hydroxy-1,1-bis(hydroxymethyl)ethyl)amino]ethanesulfonic acid (TES), 3-[N,N-Bis(2-hydroxyethyl)amino]-2-hydroxy-1-propanesulfonic acid (DIPSO), 4-(N-Morpholino)butanesulfonic acid (MOBS), 2-Hydroxy-3-[tris(hydroxymethyl)methylamino]-1-propanesulfonic acid (TAPSO), 4-(2-Hydroxyethyl)piperazine-1-(2-hydroxypropanesulfonic acid hydrate (HEPPSO), Piperazine-1,4-bis(2-hydroxypropanesulfonic acid)dihydrate (POPSO), 4-(2-25 Hydroxyethyl)-1-piperazine propanesulfonic acid (EPPS), N-(2-Hydroxyethyl)-piperazine-N'-(4-butanesulfonic acid) (HEPBS), [(2-Hydroxy-1,1-bis(hydroxymethyl)ethyl)amino]-1-propanesulfonic acid (TAPS), 2-Amino-2-methyl-1,3-propanediol (AMPD), N-tris(Hydroxymethyl)methyl-4-aminobutanesulfonic acid (TABS), N-(1,1-Dimethyl-2-hydroxyethyl)-3-amino-2-hydroxypropanesulfonic acid (AMPSO), 2-(Cyclohexylamino) ethanesulfonic acid (CHES), 3-(Cyclohexylamino)-2-hydroxyl-1-propanesulfonic acid (CAPSO), 2-Amino-2-methyl-1-propanol (AMP), 3-(Cyclohexylamino)-1-propanesulfonic acid (CAPS), 4-(Cyclohexylamino)-1-butanesulfonic acid (CABS), 2-(N-Morpholino) ethanesulfonic acid hydrate (MES), N-(2-Acetamido)-2-aminoethanesulfonic acid (ACES), and mixtures of two or more thereof.

The neutralizers may include but are not limited to sodium thioglycollate, sodium thiosulfate, catalase, sodium bisulfate, sodium bisulfite lecithin, polysorbate 20, polysorbate 80, calcium bicarbonate, and mixtures of two or more thereof.

The agents for maintaining osmotic equilibrium may include sodium salt, potassium salts, magnesium salts, manganese salts, calcium salts, other, e.g., transition metal salts, sodium chloride, potassium chloride, magnesium sulfate, iron chloride, and mixtures of two or more thereof.

In one embodiment, the incubation medium comprises an aqueous composition comprising: water; from about 0.01 to about 100 grams per liter of water (g/l), and in one embodiment from about 0.1 to about 50 g/, of one or more nutrient sources; from about $1.0 \times 10^{-5}$ to about 10 g/l, and in one embodiment from about $1.0 \times 10^{-4}$ to about 1.0 g/l of one or more microbial growth indicators; up to about 5000 g/l, and in one embodiment from about 0.001 to about 5000 g/l, and in one embodiment from about 0.1 to about 1000 g/, of one or more pH buffers; up to about 100 g/l, and in one embodiment from about 0.01 to about 100 g/l, and in one embodiment from about 0.1 to about 50 g/l, of one or more neutralizers; up to about 50 g/l, and in one embodiment from about 0.1 to about 50 g/l, and in one embodiment from about 0.1 to about 25 g/l, of one or more agents for maintaining osmotic equilibrium.

The incubation medium may comprise a nutrient broth, D/E neutralizing broth, Davis minimal medium, sterility test broth, as well as any soybean-casein digest or beef extract based media. These may include an aqueous solution of soybean-casein digest broth, fluid thioglycollate and Dextrose Tryptone (Difco Laboratories, Inc.). A modified tryptic soy broth base, without glucose, may be used. A membrane potential dye or voltage sensitive dye may also be added.

An example of an incubation medium that may be used is Bacto™ Tryptic Soy Broth which contains pancreatic digest of casein (17.0 g/l), enzymatic digest of soybean meal (3.0 g/l), sodium chloride (5.0 g/l), dipotassium phosphate (2.5 g/l), and dextrose (2.5 g/l. These ingredients may be dispersed or dissolved in water. The concentrations expressed in terms of g/l refer to grams of ingredient per liter of water. Pancreatic digest of casein, enzymatic digest of soybean meal, and dextrose provide energy sources for growth of the microorganism. These may be referred to as nutrient sources. Sodium chloride may be used to maintain an osmotic equilibrium in the liquid medium. Dipotassium phosphate may act as a pH buffer. $DiOC_6(3)$, for example, which is a membrane potential dye, may be added (3 μg/l) to the Bacto™ Tryptic Soy Broth formulation.

The incubation medium may comprise a very basic formulation that may serve only to enhance ion flux events and/or to initiate the germination of spores. This medium may comprise amino acids, salts, and/or sugars. Examples of amino acids include L-alanine, L-leucine, L-cysteine, L-valine, L-lactate, L-threonine, L-tartaric acid, folic acid, L-tyrosine, L-proline, and asparagine. Examples of salts are sodium chloride and potassium chloride. Examples of sugars include glucose, sucrose, fructose, and xylose. Additional ion flux events or germination events may be triggered by components found in the supernatant of growing organisms such as peptidoglycan and muropeptides.

Membrane potential dyes are fluorescent and therefore the detection method of choice must have the ability to distinguish between fluorescence from the dye molecules that are bound within the membrane versus fluorescence from free dye molecules. Two methods particularly suited for distinguishing between the fluorescence emissions from these two sources are fluorescence polarization (also known as fluorescence anisotropy) and fluorescence resonance energy transfer based (FRET-based) techniques, including time resolved FRET.

Fluorescence polarization is a detection method that relies on changes in the apparent size of a fluorescent molecule for detection. Polarization measurements may be based on the principle of selective excitation of fluorophores by polarized light. Fluorophores have transition moments for absorption and emission that lie along specific orientations with respect to the molecular axes of the fluorophore and will preferentially absorb photons whose electric vectors are aligned parallel to these transition moments. In an isotropic solution, the fluorophores may be oriented randomly. Upon excitation with polarized light, those fluorophore molecules whose absorption transition dipole is parallel to the electric vector of the excitation may be preferentially excited. This selective excitation may result in a partially oriented population of fluorophores and further resulting in a partially polarized fluorescence emission. Emission also occurs with the light polarized along a fixed axis in the fluorophore. Fluorescence polarization may excite molecules with plane-polarized light. The emitted light may then be measured in both the initial plane-polarized position and in a position offset from the plane-polarized light, usually offset by 90°. For example, if the electric vector of the excitation light is vertically plane-polarized, then the emitted light may be measured in both the vertical and horizontal positions. Fluorophores which are "aligned" with the electric vector of the excitation light will preferentially absorb the light: The emitted light may then be measured in both the horizontally polarized position and the vertically polarized position. Polarization may be expressed as a ratio of the light intensities and is a measure of the extent of molecular rotation during the period between excitation and emission. Small molecules may rotate faster and would have a lower intrinsic polarization value than larger molecules. Larger molecules, on the other hand, may rotate less and therefore have a higher intrinsic polarization value. By using fluorescence polarization, it may be possible to distinguish between bound membrane potential dyes and unbound membrane potential dyes.

An incubator/reader based on fluorescence polarization may be designed as shown in FIG. 2. FIG. 2 is a schematic illustration of a fluorescence polarizer. Referring to FIG. 2, incubator/reader 100, which provides for the testing of sample 110, includes monochromatic light source 120, beam splitter 130, and polarizers 140, 150 and 160. Monochromatic light from the monochromatic light source 120 passes through polarizer 140 so that all the excitation light is polarized. This polarized light then preferentially excites only the molecules in the sample 110 that are in the same polarization state as the filter. As these molecules rotate, they move out of the plane polarized position. The emitted light is split by beam splitter 130. The beam splitter splits the light and passes approximately half the light through polarizer 150 oriented in the same plane as the excitation light and the other half through polarizer 160 oriented at an angle to the initial excitation light. The light passed through each polarizer 150 and 160 is measured and compared.

Fluorescence resonance energy transfer (FRET) is the transfer of energy from an initially excited donor fluorophore to an acceptor fluorophore. The donor fluorophore typically emits at a shorter wavelength which overlaps with the absorption spectrum of the acceptor. Resonance energy transfer occurs without the appearance of a photon and is the result of long-range dipole-dipole interactions between the donor and acceptor fluorophores.

To monitor changes in membrane potential with FRET, two fluorophores are required. The FRET donor could be any fluorophore that would provide a sufficient absorption spectrum for the acceptor. The acceptor fluorophore would be the membrane potential dye. Preferably the donor fluorophore would attach or adhere to the spore wall enabling close proximity with the membrane potential dye. Otherwise, the fluorescence detection (FRET) option would be monitored by the same type of fluorometer described elsewhere herein and in the provided examples.

In addition to membrane potential dyes, voltage-sensing or voltage-sensitive dyes can detect the same changes in the membrane potential of organisms using yet another set of principles. The use of voltage-sensitive dyes for the detection of membrane potential is based on the physical mechanism known as electrochromism. Both the excitation and emission spectra of these dyes exhibit significant shifts due to voltage changes. These shifts in spectra arise from charge rearrangements that mirror membrane potential changes. The most commonly used class of voltage-sensitive dyes are the styryl dyes, specific examples include di-8-butyl-amino-naphthyl-ethylene-pyridinium-propyl-sulfonate (di-8-ANEPPS) and di-4-butyl-amino-naphthyl-ethylene-pyridinium-propyl-sulfonate (di-4-ANEPPS).

The use of voltage-sensitive dyes in combination with a FRET-type technique enables the easy detection of changes in membrane potential. For example, as charge rearrangements occur in the membrane of germinating organisms such as spores, the emission wavelength of the voltage-sensitive dyes will begin to shift. This shift in emission wavelength can then be detected by a second fluorophore located in the culture media. The emission from this second wavelength can be detected by the detector. For example, the peak in the excitation spectra for di-8-ANEPPS shifts between 450 nm and 520 nm depending on the voltage/charge characteristics. This results in a corresponding peak shift in the emission spectra from 530 nm to 640 nm. The fluorometer/incubator may be designed to excite di-8-ANEPPS at either 450 nm or 520 nm and then detect a second fluorophore that has an excitation peak at the corresponding emission peak of the di-8-ANEPPS.

An alternative detection method for the detection of membrane potential changes is the use of electronic signals. As organisms such as spores begin to germinate, the membrane potential will increase allowing for more current flow and greater voltage drops resulting in an increase in ion transport, which is observed as an increase in current flow, from the increased membrane potential. Electronic leads can be placed into media or across/within a biological indicator substrate to electrically measure the membrane potential. Three potential designs for biological indicators measuring electrical signals are shown below in FIGS. 3-5. Referring to FIG. 3, a biological indicator 200 is placed in media 202 which is contained in a vessel 204. Electronic leads 206 and 208 are placed in the media 202 and used to measure the membrane potential. Referring to FIG. 4, electronic leads 210 and 212 are used to measure membrane potential across a biological indicator 214. Referring to FIG. 5, electronic leads 220 and 222 are used to measure membrane potential within a biological indicator 224.

The sterilization indicator may comprise an electrically conductive material positioned on a substrate (e.g., an electrically conductive material such as a copper circuitry formed on a non-conductive substrate such as silicon) and a biological indicator (e.g., spores) positioned on part or all of the conductive material. For example, the biological indicator (e.g., spores) and an electronic circuitry or conductive digital pattern comprising a conductive material (e.g., copper) may be deposited on a non-conductive substrate (e.g., a silicon substrate) using an ink jet printer such as a Dimatix Materials Printer DMP-2800 which is available from Fuji Film. The electronic circuitry or conductive digital pattern may be deposited on the substrate using any desired pattern. The biological indicator may then be deposited on part or all of the electronic circuitry or conductive digital pattern using the ink jet printer. The biological indicator may be dispersed in a liquid vehicle or medium (e.g., water) which may then be deposited on part or all of the electronic circuitry or digital pattern with droplets as small as about 5 picoliters, or about 10 picoliters. Typical spore volumes may be about 3 picoliters per spore.

The biological indicator may be evaluated electrically by monitoring voltage (potential), current flow, resistance and/or impedance as viable organisms (e.g., spores) begin to germinate. The choice of measurement method will dictate the electronics design. An advantage includes a decrease in the time required to read the biological indicator. Since the detection method relies on one of the earliest steps in the cascade of organism germination events rather than on outgrowth or specific reporter enzymes, the detection time can be greatly reduced.

Figure 6:
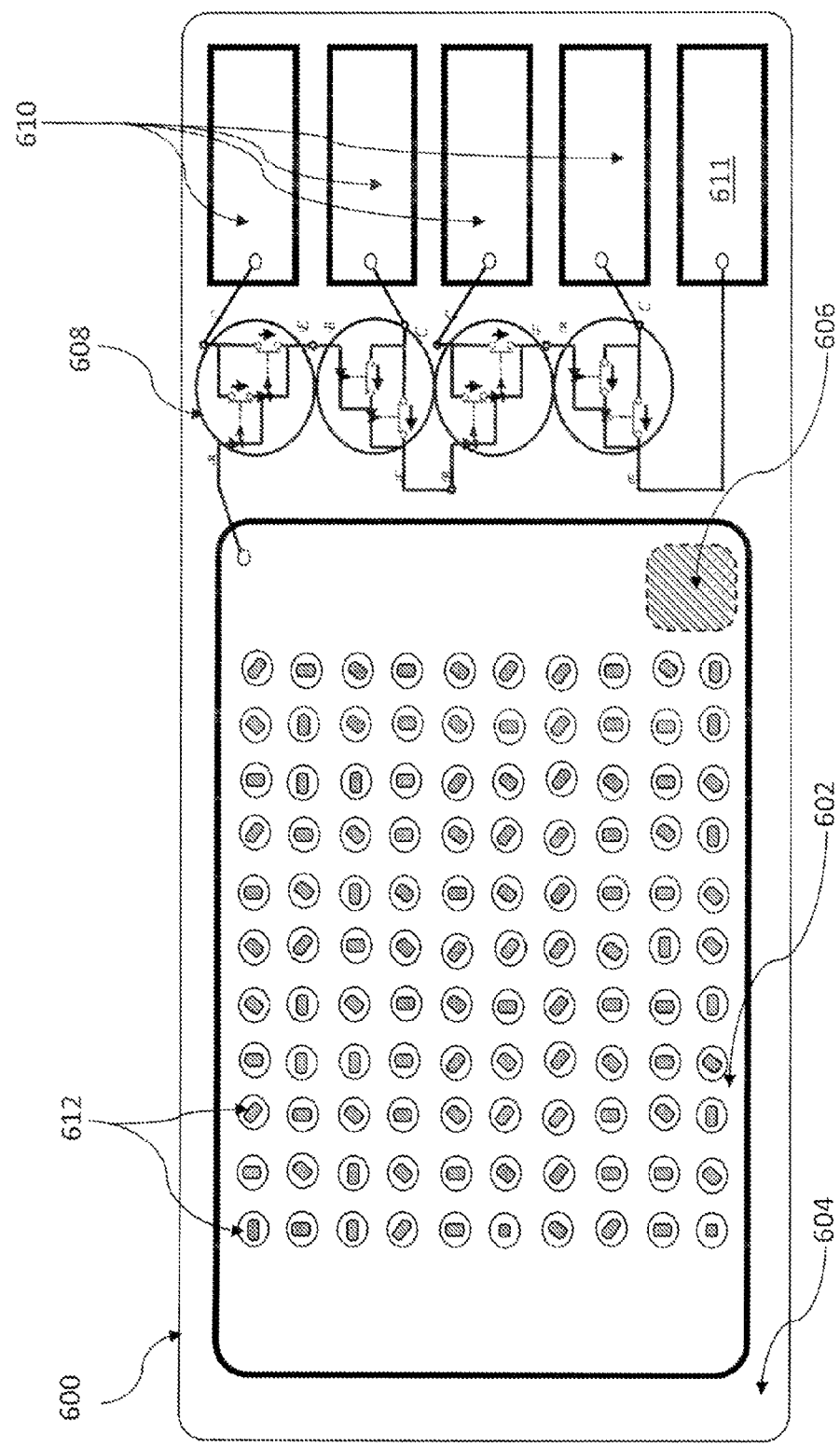
FIG. 6 is a schematic depiction of bottom element of an electrical embodiment of a sterilization indicator in accordance with the present invention.

FIG. 6 is a schematic depiction of bottom element 600 of an electronic version of a sterilization indicator in accordance with an embodiment of the present invention, such as that shown in FIGS. 4 and 5. FIG. 6 shows the elements of the bottom element 600 of the sterilization indicator in more detail. The bottom element 600 includes an electrically conductive material 602, such as a monolayer of polyacrylamide/polyaniline, positioned on a non-conducting substrate 604. The electrically conductive material 602 may include any suitable material as long as the material is suitable for use with the sterilization conditions with which the sterilization indicator will be used. The non-conducting substrate 604 may be any suitable gas/liquid impermeable substrate material such as PET or other suitable material that is suitable for use in the sterilization conditions with which the sterilization indicator will be used. As shown in FIG. 6, positioned between the conductive material 602 and the layer 604 is a conducting underlayer 606, which is in electrical communication with the conductive material 602 and detection circuitry. The detection circuitry includes a series of serial transistor preamplifiers 608, which are electrically connected to electrical connectors 610 and to the ground connector 611. The electrical connectors 610 provide electrical communication from the bottom element 600 to a reader device, described below. The preamplifiers 608 provide stepwise amplification of changes in electrical current passing through the sterilization indicator, as described in more detail below. By having a series of amplifiers, a signal from the biological indicator card can be suitably amplified without the introduction of excessive noise. The circuit is completed by the ground connector 611.

As shown in FIG. 6, spores 612 of a suitable test organism may be deposited on or embedded in the conducting monolayer 602. The spores 612 may be deposited as individual spores or as multiple spores. The spores 612 may be deposited, for example, in a polyacrylamide/buffer mixture, in which case the spore is considered to be within a "bubble" of the buffer material, which "bubble" is embedded in a matrix such as polyacrylamide. Alternatively, the spores 612 may be embedded directly into a layer of, e.g., polyaniline.

Figure 7:
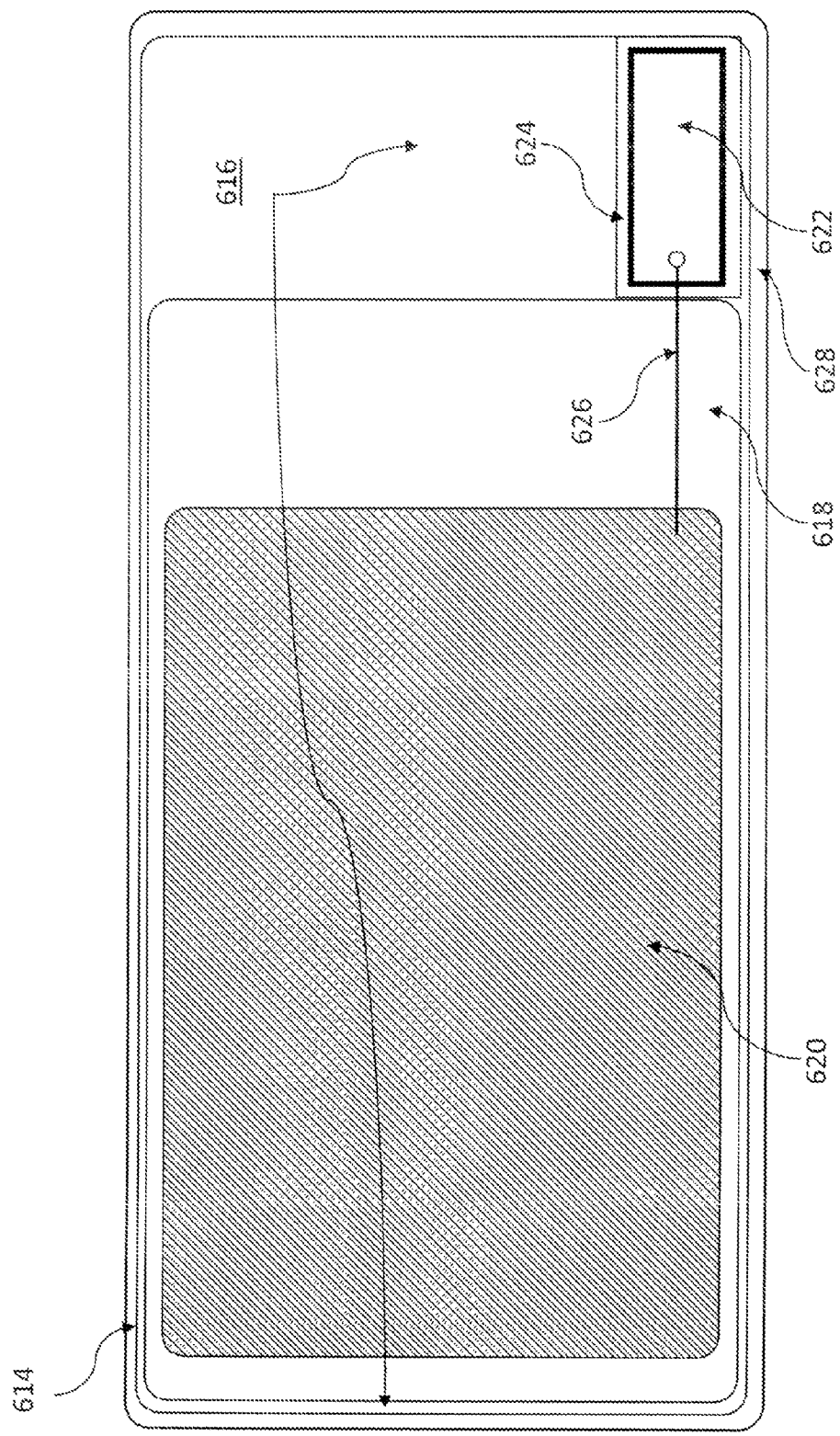
FIG. 7 is a schematic depiction of top element of an electrical embodiment of a sterilization indicator in accordance with the present invention, such as that of FIG. 6.

Referring now to FIG. 7, which is a top plan view of an top element 614 for the sterilization indicator, additional details of this embodiment of the invention are shown. The side of the top element 614 shown in FIG. 7 is the side that will face and contact the upper layer of the structure shown in FIG. 6. The top element 614 includes a removable gas/liquid impermeable protective membrane 616, on which is formed a gas/steam permeable layer 618. Overlaying the permeable layer 618 is a conductive layer 620. When the sterilization indicator is assembled, the conductive layer 620 will be in electrical communication with the spores 612 and any surrounding conductive material such as the conductive monolayer 602, and will also be in electrical communication with a connector 622 via the lead 626. As shown in FIG. 7, the connector 622 is positioned beneath an insulator pad 624. The connector 622, via the wire 626, will complete the electrical circuit formed by the conductive layer 620, the spores 612, the conductive underlayer 606, the preamplifiers 608 and the connectors 610. Changes in the flow of current through this electrical circuit will be used to detect whether any test organisms have survived the sterilization process in which the sterilization indicator 600 will be used. As shown in FIG. 7, the top element 614 includes an adhesive line 628, by which the top element 614 will be sealingly attached to the bottom element 600, thus forming the sterilization indicator of this embodiment.

Prior to use of the sterilization indicator, the gas/liquid impermeable protective membrane 616 will remain in place to protect the sterilization indicator 600 from exposure to the environment. Just before the sterilization indicator is to be used in a sterilization process, the membrane 616 will be removed to allow the sterilization medium to reach the spores 612 in the sterilization indicator.

Figure 8:
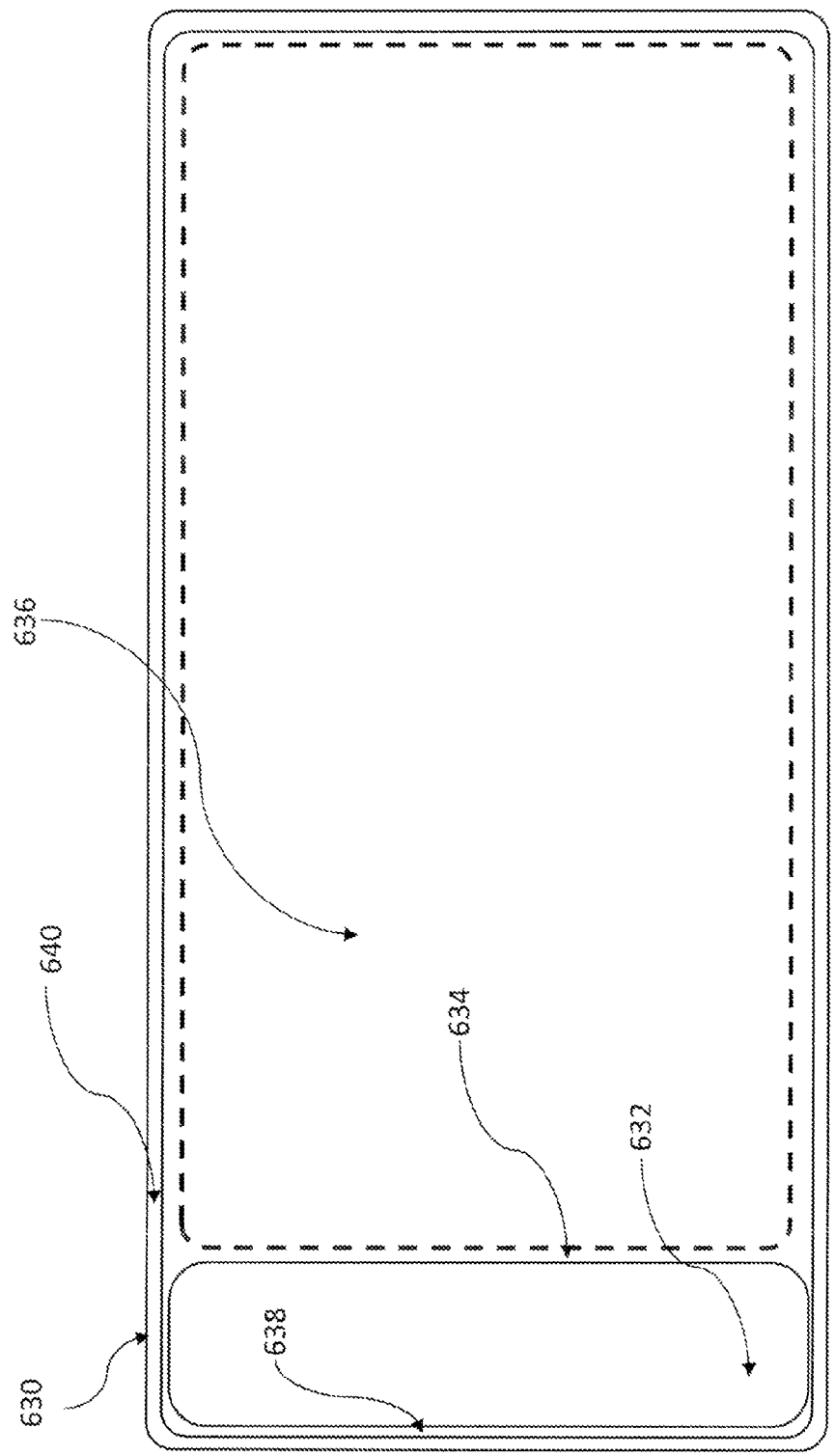
FIG. 8 is a schematic top plan view of a top seal layer for use with an embodiment of the present invention, such as those of FIGS. 4-7.

FIG. 8 is a schematic top plan view of a top seal layer 630 for use with an embodiment of the present invention, such as those of FIGS. 4-7. In the embodiment shown in FIG. 8, the top seal 630 includes a fluid filled chamber 632 containing a thermally stable inducer and media to activate and support the underlying spores 612. the fluid filled chamber 632 is connected to the remainder of the top seal layer 630 by a frangible break-away zone 634, by which the chamber can be removed from the remainder of the top seal 630. The top seal 630 further includes a window 636 communicating with the gas/liquid permeable layer 618 of the top element 614. The top seal 630 further includes a thermal weld 638 and a peelable adhesive zone 640, for attaching the top seal 630 to the top element 614. The thermal weld 638 attaches the chamber 632 to the top element 630.

Figure 9:
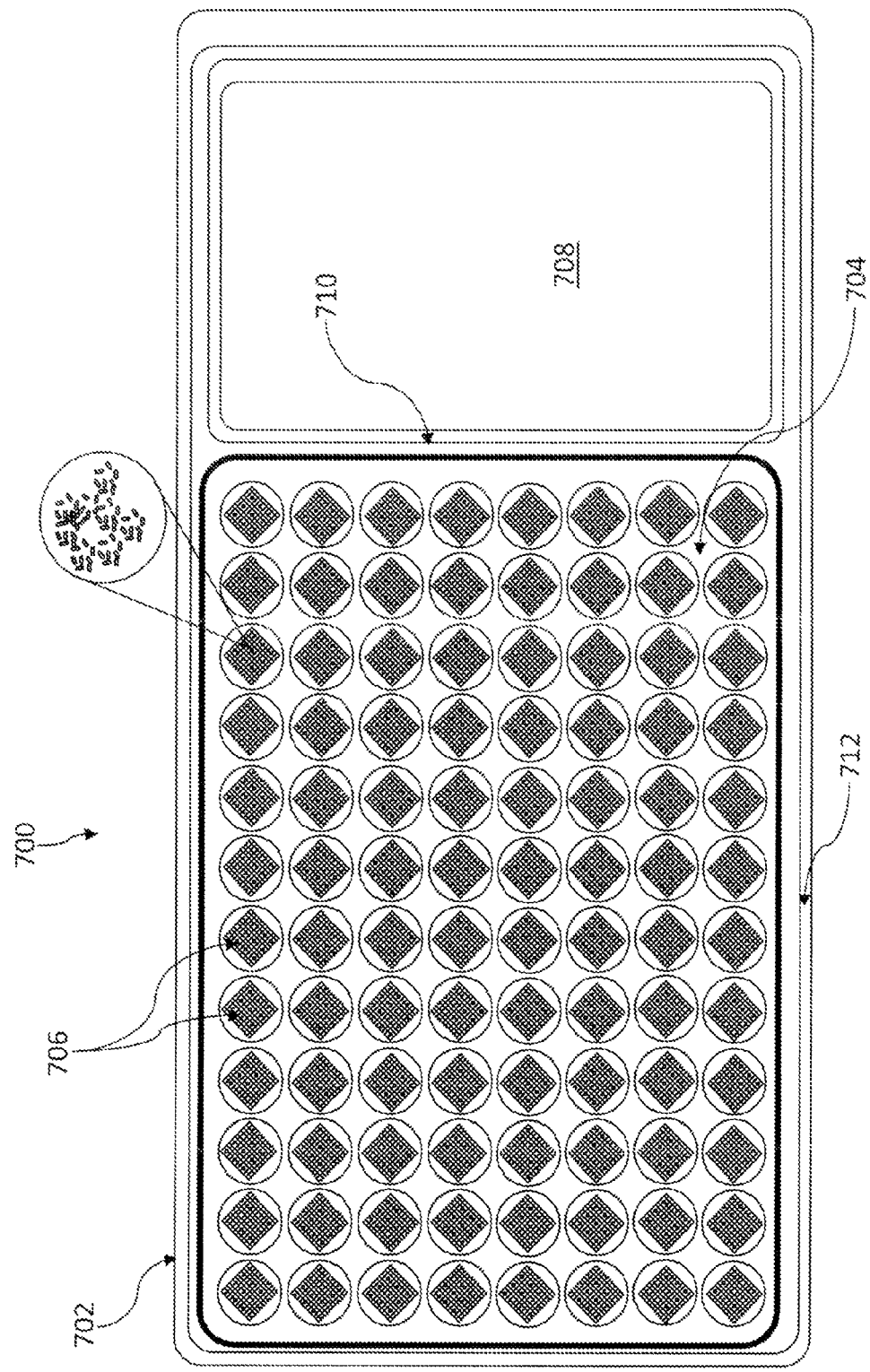
FIG. 9 is a schematic top plan view of a bottom element 700 of another embodiment of the present invention, which is a fluorescent-based embodiment of a sterilization indicator.

FIG. 9 is a schematic top plan view of a bottom element 700 of another embodiment of the present invention, which is a fluorescent-based embodiment of a sterilization indicator. The sterilization indicator shown in FIG. 9 relies upon fluorescence generated by growing spores as the indication of success or failure of the sterilization process.

In the embodiment shown in FIG. 9, the bottom element 700 includes a backing substrate 702 to which the overlying materials or elements will be deposited. The backing substrate 702 may be any suitable gas/liquid impermeable material, such as PET (e.g., Mylar®), polypropylene, metal or lacquered foil or any suitable polyolefin known to be useful with a sterilization indicator by those of skill in the art. Deposited on the backing substrate 702 is a hydrating monolayer 704. The hydrating monolayer 704 may be, e.g., polyacrylamide, and may have added attachments for spores, or the spores may be embedded in the hydrating monolayer 704. The bottom element 702 will be covered by a gas/steam permeable, fluorescence wavelength transparent seal (not shown), which will be adhered or welded to the bottom element 702. The transparent seal will allow ingress of sterilization medium to the spores of the test organism and will allow passage of the excitatory and fluorescence wavelengths used for reading the sterilization indicator.

In the embodiment illustrated in FIG. 9, the spores are applied in 10×10 grids 706 of "spots" of spores. Each spot may contain, e.g., from about 150 to about 300 spores. In the embodiment in FIG. 9, there is a 8×12 array of the 10×10 grids. Since each spot contains about 150 to about 300 spores, there are 100 spots in each of the 96 elements of the array, there are from about $1.44 \times 10^6$ to about $2.88 \times 10^6$ spores present on the sterilization indicator shown in FIG. 9.

The embodiment illustrated in FIG. 9 further includes a fluid filled chamber 708 which contains, e.g., thermally stable inducer and media needed to activate and support the spores which will generate fluorescent events to be detected. The fluid filled container 708 is attached to the remainder of the bottom element 700 by a frangible break-away zone 710. When the frangible break-away zone 710 is broken, the contents of the container 708 are provided to the spores in the grids 706.

The bottom element 700 further includes a perimeter adhesive line 712 by which the gas/steam permeable cover (not shown) is sealingly attached to the bottom element.

Figure 10:
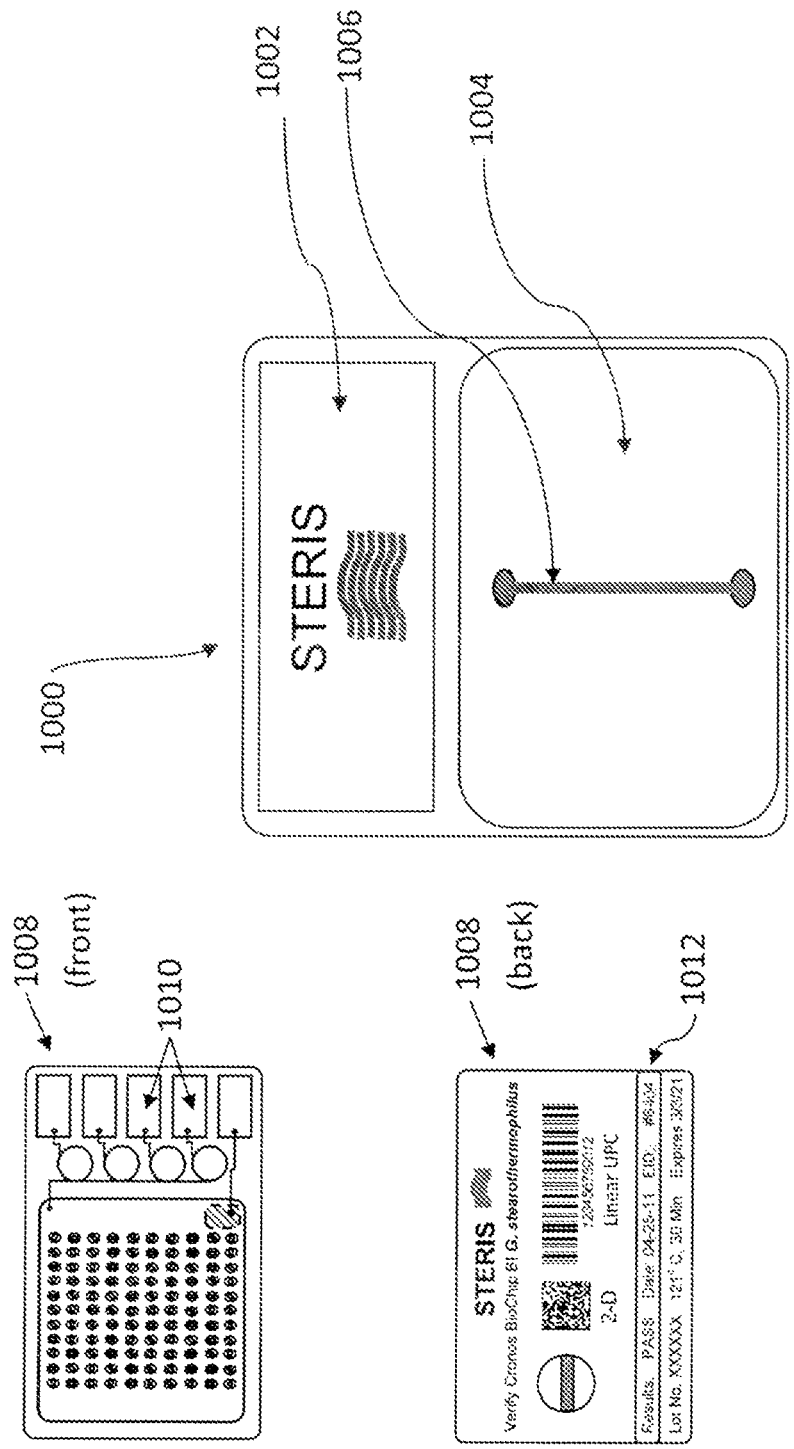
FIG. 10 is a schematic front view of a reader for use with an electronic-based version of a sterilization indicator in accordance with an embodiment of the present invention, together with front and back views of an exemplary electronic sterilization indicator card.

FIG. 10 is a schematic front view of an electronic reader 1000 for use with an electronic-based version of a sterilization indicator in accordance with an embodiment of the present invention, together with front and back views of an exemplary electronic sterilization indicator card, such as that of FIG. 6. The electronic reader 1000 includes a front display panel 1002 for displaying relevant information obtained from its reading of the biological indicator card. The electronic reader 1000 further includes a front access panel 1004 and a slot 1006 for inserting a biological indicator card. FIG. 10 also includes a depiction of an exemplary electronic version of a biological indicator card 1008, which includes the biological and electronic components such as described above with respect to FIG. 6, including the electrical connectors 1010.

The electronic reader 1000 includes suitable electronic components to make contact with the electrical connectors 1010 of the biological indicator card 1008. The front access panel 1004 may include integrated rollers or the like to activate a fluid reservoir and heater for incubation.

FIG. 10 shows both a front view and a back view of the exemplary electronic biological indicator card 1008. The components of the front view have been described generally with respect to the embodiment of FIG. 6. The back side of the indicator card 1008 may include, for example, information relevant to the specific type of biological indicator, the sterilizing medium, the sterilization process parameters, the lot number, the date and outcome of the biological indicator test. The information shown on the indicator card 1008 is not limited to these specific examples; other information that may be deemed important may also be included, as will be understood. The indicator card 1008 may include a magnetic strip 1012 to facilitate automated reading and storing of information relevant to the sterilization process, test results, etc., as will be understood.

Figure 11A:
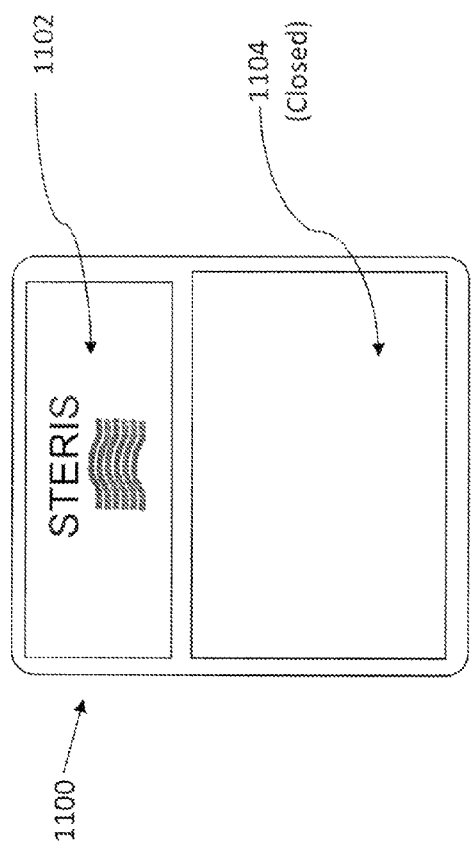
FIGS. 11A and 11B are schematic front views of a reader for use with a fluorescence-based version of a sterilization indicator in accordance with an embodiment of the present invention, in a closed and open position, respectively.
Figure 11B:
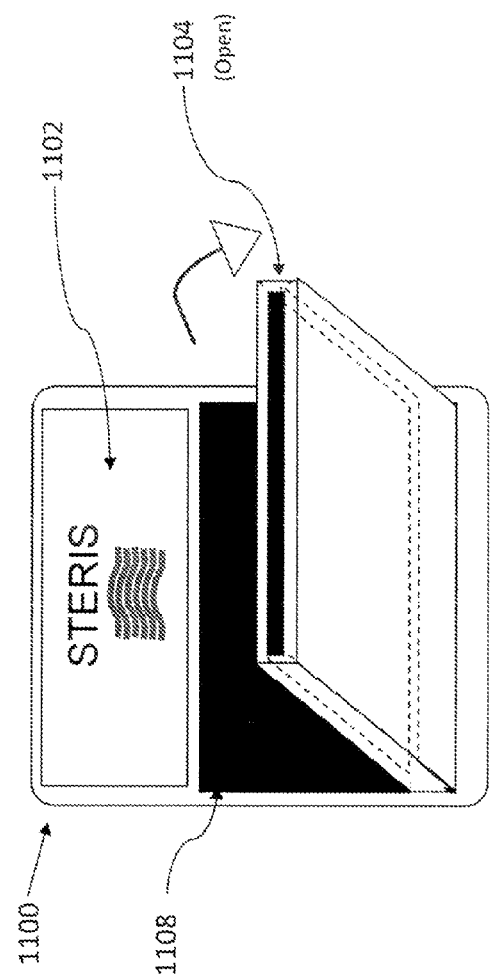

FIGS. 11A and 11B are schematic front views of a fluorescence reader 1100 for use with a fluorescence-based version of a sterilization indicator in accordance with an embodiment of the present invention, in a closed and open position, respectively. FIG. 11A shows the fluorescence reader 1100 in closed position. The fluorescence reader 1100 includes a front display panel 1102 for displaying relevant information obtained from its reading of the biological indicator card. The fluorescence reader 1100 further includes a front access panel 1104, which can open, as shown in FIG. 11B.

As shown in FIG. 11B, the front access panel 1104 opens outwardly, and includes a slot 1106 into which can be inserted a fluorescence-based biological indicator card, such as that described above with respect to FIG. 9. When an indicator card has been inserted into the slot 1106, the front access panel 1104 is closed, placing the indicator card into a reader chamber 1108, which contains components for obtaining information from the indicator card in the slot. Exemplary, suitable components of the reader chamber 1108 are described with respect to FIG. 12. The front access panel 1104 may include integrated rollers or the like to activate a fluid reservoir and heater for incubation.

Figure 12:
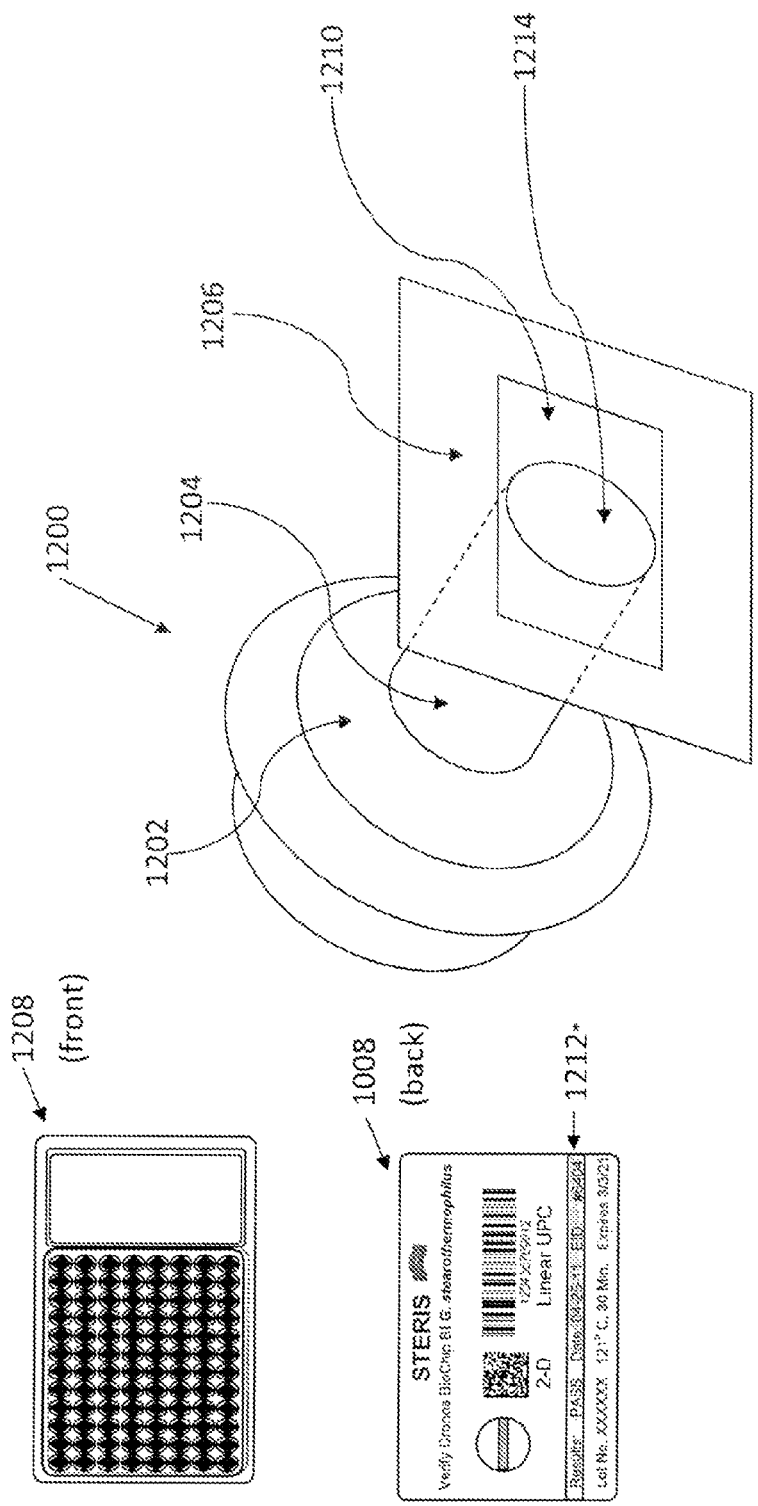
FIG. 12 is a schematic perspective view of internal components of a fluorescence reader such as that of FIG. 11, together with front and back views of an exemplary fluorescence-based sterilization indicator card.

FIG. 12 is a schematic perspective view of internal components of a fluorescence reader 1200 such as that of FIG. 11, together with front and back views of an exemplary fluorescence-based sterilization indicator card.

The fluorescence reader 1200 includes suitable components for reading a fluorescence-based sterilization indicator. Some exemplary components are illustrated in FIG. 12. The reader 1200 may include a suitable reading device such as a cooled CCD (charge-coupled device) camera and image processor 1202, including suitable hardware and software for processing data obtained from the CCD camera. The reader 1200 may include suitable optics 1204, such as a LED exciter and fluorescence detector. The reader 1200 may include suitable mechanical components 1206, such as a camera board, LED control and USB interface. The reader 1200 may further include suitable apparatus 1210 for holding the biological indicator card, for aligning the card and holding it in registered position for excitation and reading. The reader 1200 may further include a suitable image scanning port 1214.

FIG. 12 shows both a front view and a back view of the exemplary electronic biological indicator card 1208. The components of the front view have been described generally with respect to the embodiment of FIG. 9. The back side of the indicator card 1208 includes various information relevant to the specific type of biological indicator, the sterilant, the sterilization process, the lot number, the date, sterilization conditions and outcome of the biological indicator test. The information shown on the indicator card 1208 is not limited to these specific examples; other information that may be deemed important may also be included, as will be understood. The indicator card 1208 may include a magnetic strip 1212 to facilitate automated reading and storing of information relevant to the sterilization process, test results, etc., as will be understood.

Figure 13:
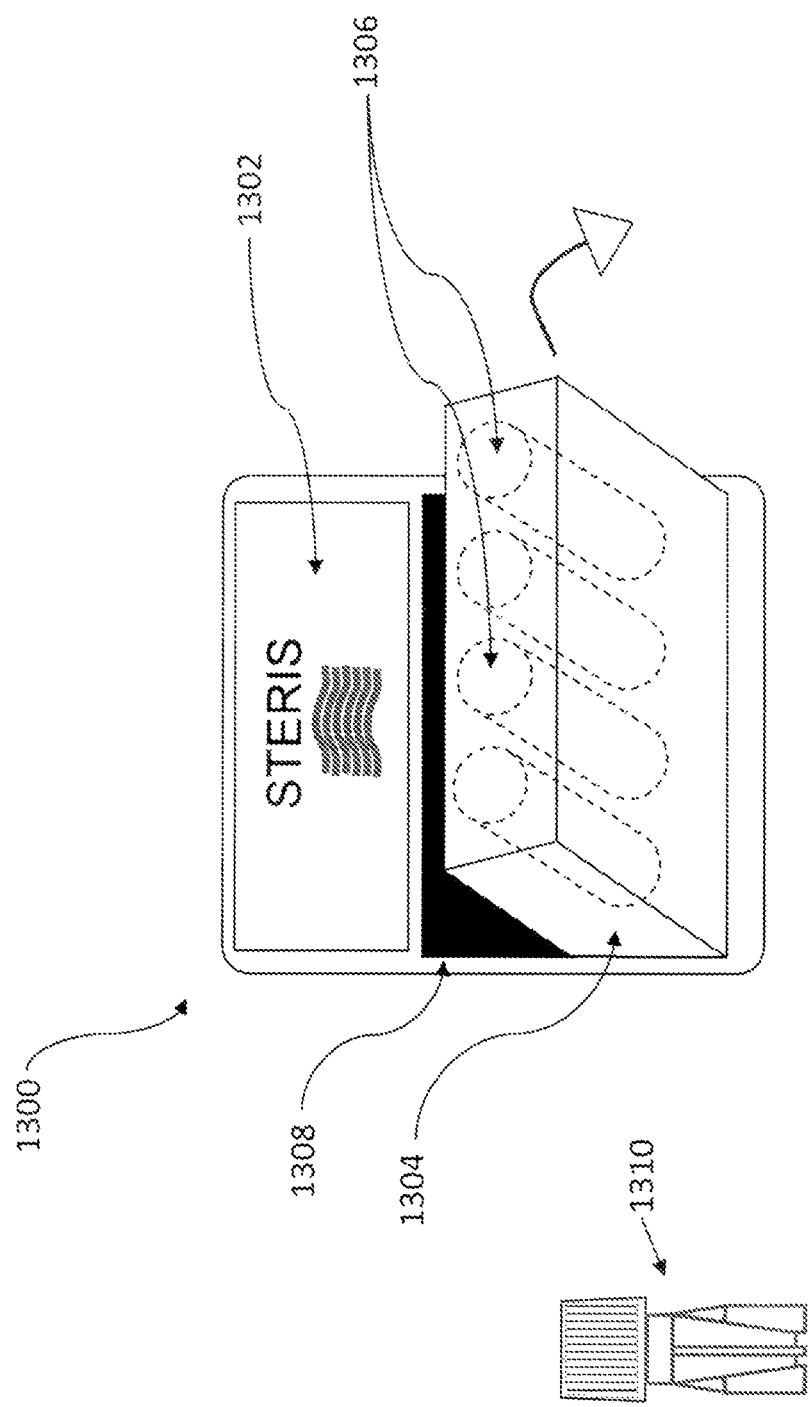
FIG. 13 is a schematic front view of a reader for use with a FABI self-contained biological indicator.

FIG. 13 is a schematic front view of a vial reader 1300 for use with a FABI self-contained biological indicator (SCBI), such as that described and shown with respect to FIG. 3. The vial reader 1300 includes a front display panel 1302 and a front access panel 1304, similar to those of the electronic-based and fluorescence-based embodiments described above. The front access panel 1304 includes a plurality of wells 1306, into which SCBIs can be inserted. The front access panel 1304 pivots outwardly, to allow insertion or removal of SCBIs and is closeable into a reader chamber 1308. The vial reader 1300 may be used with a fluorescence-based SCBI or with an electronic-based SCBI, applying the same basic principles as disclosed herein for reading the results of the sterilization process and indicated by the biological indicator of the present invention. FIG. 13 includes an exemplary FABI SCBI 1310.

With the inventive method, a change in the membrane potential of a viable organism may be used to evaluate the effectiveness of the sterilization process. This technique may be used with a suitable sterilization indicator or SCBI as known in the art. It may also be used with an organism (e.g., spore) suspension in an ampoule. It may also be used with a sterilization indicator comprising an electrically conductive material positioned on a substrate (e.g., copper circuitry formed or deposited on a non-conductive substrate such as silicon) with a biological indicator (e.g., bacterial spores) positioned on part or all of the conductive material. The inventive method is flexible enough to be used across all sterilization technologies. The inventive method may be used to provide for instant-read or near-instant read biological indicators. The biological indicator may be referred to as a fast-acting biological indicator.

Examples of materials of construction throughout: Supports, Separators and or Insulators: Glass, silicon, metal foils, paper and other cellulosic forms, polyolefin including polypropylene, polycarbonates or blends, cellulose acetate, Mylar and the like. Semi-permeable or permeable membranes: Glassine, dialysis membranes of natural or synthetic origin, porous polyolefin and other plastic materials. Conductors: metals, foils, conductive inks, nanotubes, fullerenes and the like. Switchable conductors/insulators or other semi-conducting materials like polyaniline and the like. Attachment chemistries (e.g. SPDP and the like). Organisms: including *G. stearothermophilus*, *B. atrophaeus* and the like. Fluorophores and or fluorogens, e.g., MUG and propidium iodide, fluorescein, rhodamine etc. including all that respond to physical excitations like photo-excitation, chemical induction and electro-physical activation.

In one embodiment, plasma membrane potential is the sole means of detection. In another embodiment, detection is by both membrane potential and by electrically induced fluorescence (e.g., using di-4-ANEPPS or the like). The ANEP (AminoNaphthylEthenylPyridinium) dye, di-4-ANEPPS is a sensitive probe for the detection of sub-millisecond membrane potential changes. In this latter case a reader would be a hybrid of an electronically-based reader such as that of FIG. 10, and a fluorescence-based reader such as that of FIG. 12. In one embodiment, fluorescence of a fluorogenic compound after induction and enzymatic activation may be the sole means of detection. In another embodiment, a second surface bound fluorophore (e.g. Texas red WGA) may also be used, which would provide continuous fluorescence as both a reference control and as a means to ensure that all the spores are still associated with the biological indicator card. Each fluorophore may have separate emission and excitation wavelengths.

EXAMPLES

The examples provided here are for illustrative purposes only. They are intended to provide sufficient composite detail to enable a person of skill in the art to make and use the present invention and to provide illustrative examples of suitable devices and methods. The preferred embodiment may comprise part or all of the materials, components, methods or applications described herein; but are not limited to just those presented. Simple substitutions may be performed that may alter the component list or application utility but these too are contemplated. The final production device may take the form of one or another of the presented embodiments, with one or more of the described options, but the exemplified' configurations do not constitute abandonment of any other variation or mode of action that one skilled in the art might extend to the disclosed invention.

Example 1

The evaluation of membrane potential changes in live/dead *Bacillus atrophaeus* spores illustrates the correlation between membrane potential changes and viability. The membrane potential is measured using DiOC6(3) and a Picofluor fluorometer. Both viable and non-viable spores (autoclaved) are incubated in tryptic soy broth and DiOC6(3) at 37° C. for representative times. At the indicated incubation times, the organisms are removed and washed in Tris/EDTA (pH 7.4). Fluorescence measurements are then taken. The results are shown in FIG. 1.

Example 2

Electrical Detection of Viable *Geobacillus stearothermophilus* Spores on a Flat Surface A conducting metalized material is cast uniformly onto a non-conducting Mylar sheet approximately the size of a credit card. The mylar sheet is both gas and liquid impermeable. A polyacrylamide/polyaniline mixture is cast on top of the metalized layer. The polyacrylamide/polyaniline mixture is permeable to both gas and steam. *Geobacillus stearothermophilus* spores are re-suspended in polyacrylamide/polyaniline mixture at a concentration of $10^8$ cfu/ml. This spore concentration gives a single spore in each 10 pL (picoliter) drop from an ink jet printer. The spore polyacrylamide/polyaniline mixture is deposited onto the cast polyacrylamide/polyaniline film in an array format. A second conducting metalized material is cast over the array of spores. This forms the biological indicator (BI) card. As the spores germinate, the conductivity of the material will begin to increase. The current flow is detected by serial transistor preamps such as Darlington couples. Because these Darlington transistors are paired they enable the amplification of the current. The Darlington transistors are connected to leads that monitor the current of the system. A gas barrier, such as mylar, is adhered to the top of the indicator by a peelable adhesive until just before use, At the time of use this barrier is removed so that steam or gas may penetrate the system when placed into a sterilizer. At the far end of the indicator is a small frangible chamber containing incubation media that will enable viable spores to germinate. Following a sterilization process utilizing steam or vaporous hydrogen peroxide the biological indicator is incubated.

The BI card is inserted into the card reader/incubator slot that is integrated into a sterilizer. The reader/incubator consists of heating blocks to maintain the incubation temperature, electrical connections in which the BI card connects, print head to mark cycle parameters and Load ID in a user readable form, rollers to guide the BI card into the slot and to automatically activate the BI by breaking the frangible chamber containing the incubation media and aiding in the medium dispersal, a magnetic strip scanner, and a bar code reader to track the results of the BI card back to the device load and sterilization cycle.

The indicator is incubated at 55-60° C. (optimal temperature for *Geobacillus stearothermophilus*) and the conductance of the indicator is monitored. Small changes in current resulting from germinating viable spores are detected in a matter of minutes alerting the user that their sterilization process may not have been successful. If the sterilization process was successful, there would be no increase in the measured current with incubation time.

Example 3

Fluorescence Detection of Viable *Geobacillus stearothermophilus* Spores on a Flat Surface A polyacrylamide layer is cast onto a polypropylene backing approximately the size of a credit card. The polyacrylamide layer acts as a hydrating monolayer. *Geobacillus stearothermophilus* spores are then printed in spots of organisms. The spots are printed in an array or grid format with each spot containing between 150-300 spores. At one end is a frangible chamber containing the incubation media with the required fluorophore(s). At the completion of the sterilization process the BI card is inserted into the card reader/incubator slot that is integrated into a sterilizer. The reader/incubator consists of heating blocks to maintain the incubation temperature, LED excitation sources, photodiodes for fluorescence detection, print head to mark cycle parameters and Load ID in a user readable form, rollers to guide the BI card into the slot and to automatically activate the BI by breaking the frangible chamber containing the incubation media and aiding in the medium dispersal, a magnetic strip scanner, and a bar code reader to track the results of the BI card back to the device load and sterilization cycle.

The indicator is incubated at 55-60° C. (optimal temperature for *Geobacillus stearothermophilus*). An off-the-shelf imager, such as the LumiSens, can be employed in this reader. This will enable the detection of two or more wavelengths of interest. One wavelength will measure the stained spores to ensure that all controls are in place and the second wavelength will measure the fluorophore used to detect viable organisms. If the sterilization process was successful, all the spores will be non-viable and the detector will only detect the fluorophore used to stain the organisms. If the sterilization process was not successful, the viable spores will be detected by two distinct fluorescence signals.

Example 4

Stand Alone Reader/Incubator

The reader/incubator can be a stand-alone unit for either of the reader/incubators described in Example 2 and Example 3. In a stand-alone unit, all the electronics are the same as the reader/incubators that are integrated into the sterilizers themselves.

While the invention has been explained in relation to specific embodiments, it is to be understood that various modifications thereof will become apparent to those skilled in the art upon reading the specification. Therefore, it is to be understood that the invention disclosed herein is intended to cover such modifications as may fall within the scope of the appended claims.

The invention claimed is:

1. A method for monitoring efficacy of a sterilization process, comprising:

(A) exposing an article to be sterilized and a biological indicator to a sterilization medium during a sterilization process, the biological indicator comprising a cell with a plasma membrane; and (B) incubating the cell in an incubation medium and measuring the membrane potential of the cell, wherein when measuring the membrane potential, zero change in the membrane potential indicates efficacy of the sterilization process and any change in the membrane potential indicates failure of the sterilization process.

2. The method of claim 1, wherein the sterilization medium comprises at least one liquid sterilant.

3. The method of claim 2, wherein the liquid sterilant comprises peracetic acid, at least one peroxide, or a mixture of two or more thereof.

4. The method of claim 1, wherein the sterilization medium comprises at least one gaseous sterilant.

5. The method of claim 4, wherein the gaseous sterilant comprises hydrogen peroxide.

6. The method of claim 5 wherein the gaseous sterilant further comprises ammonia.

7. The method of claim 1 wherein the sterilization medium comprises steam.

8. The method of claim 1 wherein the biological indicator comprises spores.

9. The method of claim 1 wherein the biological indicator comprises bacteria of the *Bacillus, Geobacillus* or *Clostridia* genera.

10. The method of claim 1 wherein the biological indicator comprises *Geobacillus stearothermophilus, Bacillus atrophaeus, Bacillus subtilis, Bacillus pumilus, Bacillus coagulans, Clostridium sporogenes, Bacillus subtilis globigii, Bacillus cereus, Bacillus circulans*, or a mixture of two or more thereof.

11. The method of claim 1 wherein the biological indicator comprises fungi, mycobacteria, protozoa, vegetative bacteria, or a mixture of two or more thereof.

12. The method of claim 1 wherein the biological indicator comprises *Aspergillus niger, Candida albicans, Trichophyton mentagrophytes, Wangiella dermatitis, Mycobacterium chelonae, Mycobacterium gordonae, Mycobacterium smegmatis, Mycobacterium terrae, Giardia lamblia, Cryptosporidium parvum, Aeromonas hydrophila, Enterococcus faecalis, Streptococcus faecalis, Enterococcus faecium, Streptococcus pyrogenes, Escherichia coli, Klebsiella (pneumoniae), Legionella pneumophila, Methylobacterium, Pseudomonas aeruginosa, Salmonella choleraesuis, Helicobacter pylori, Staphylococcus aureus, Staphylococcus epidermidis, Stenotrophomonas maltophilia*, or a mixture of two or more thereof.

13. The method of claim 1 wherein the biological indicator comprises *Geobacillus stearothermophilus*.

14. The method of claim 1 wherein the biological indicator is incubated in an incubation medium, the biological indicator being incubated in the presence of a membrane potential fluorescent dye.

15. The method of claim 14 wherein the dye is a carbocyanine.

16. The method of claim 14 wherein the dye is an oxonol.

17. The method of claim 14 wherein the dye is 3,3'-dihexyloxycarbocyanine iodine or bis-(1,3-dibutylbarbituric acid) trimethine oxonol.

18. The method of claim 1 wherein the membrane potential is measured using fluorescence polarization.

19. The method of claim 1 wherein the membrane potential is measured using fluorescence resonance energy transfer.

20. The method of claim 1 wherein the cell is a spore of *Geobacillus stearothermophilus*.

21. The method of claim 1 wherein the incubation medium comprises one or more nutrient sources and one or more microbial recovery, induction or growth indicators.

* * * * *